United States Patent
Fisk et al.

(10) Patent No.: US 9,039,963 B2
(45) Date of Patent: May 26, 2015

(54) TITANIUM BASED CERAMIC REINFORCED ALLOY FOR USE IN MEDICAL IMPLANTS

(71) Applicants: Andrew E. Fisk, Philadelphia, PA (US); Anatolii Demchyshyn, Kiev (UA); Mykola Kuzmenko, Kiev (UA); Sergei Firstov, Kiev (UA); Leonid Kulak, Kiev (UA)

(72) Inventors: Andrew E. Fisk, Philadelphia, PA (US); Anatolii Demchyshyn, Kiev (UA); Mykola Kuzmenko, Kiev (UA); Sergei Firstov, Kiev (UA); Leonid Kulak, Kiev (UA)

(73) Assignee: Pulse Technologies, Inc., Quakertown, PA (US)

( * ) Notice: Subject to any disclaimer, the term of this patent is extended or adjusted under 35 U.S.C. 154(b) by 281 days.

(21) Appl. No.: 13/650,877

(22) Filed: Oct. 12, 2012

(65) Prior Publication Data

US 2014/0105781 A1 Apr. 17, 2014

(51) Int. Cl.
*C22C 14/00* (2006.01)
*B22D 25/06* (2006.01)
*A61L 31/12* (2006.01)
*B22D 7/00* (2006.01)
*B22D 21/00* (2006.01)
*A61L 31/02* (2006.01)

(52) U.S. Cl.
CPC .............. *A61L 31/124* (2013.01); *B22D 7/005* (2013.01); *B22D 25/06* (2013.01); *C22C 14/00* (2013.01); *B22D 21/005* (2013.01); *A61L 31/022* (2013.01)

(58) Field of Classification Search
None
See application file for complete search history.

(56) References Cited

U.S. PATENT DOCUMENTS

| | | | |
|---|---|---|---|
| 5,415,704 | A | 5/1995 | Davidson |
| 5,498,302 | A | 3/1996 | Davidson |
| 5,954,724 | A * | 9/1999 | Davidson ........................ 606/76 |
| 6,752,882 | B2 | 6/2004 | Lin et al. |
| 7,682,473 | B2 | 3/2010 | Boehlert |
| 7,892,369 | B2 | 2/2011 | Bhambri |

FOREIGN PATENT DOCUMENTS

| | | | |
|---|---|---|---|
| EP | 0 555 033 A1 | 8/1993 | |
| EP | 2 021 041 A2 | 2/2009 | |
| KR | 1020060101715 A | 9/2006 | |
| KR | 1020060101715 | 12/2006 | |
| KR | 2008 0072812 A | 8/2008 | |
| RU | 2211254 | * 8/2003 | ............. C22C 14/00 |
| WO | 2007137772 A2 | 12/2007 | |

OTHER PUBLICATIONS

Tavares A. M. G. et al. "The addition of Si to the Ti-35Nb Alloy and Its Effect on the Corosion Resistance, When Applied to Biomedical Mater." Journal of Alloys and Compounds, vol. 591, Jan. 3, 2014, pp. 91-99.
Kee-Do Woo, et al. "Microstructure and Biocompatibility of Ti-Nb-Si-HA Composites Fabricated by Rapid Sintering Using HEMM Powders." Korean Journal of Materials Research, vol. 23, No. 7, Jul. 27, 2013, pp. 353-358.
Vozilkin V. A., et al. "Precipitation of Silicides and Germanides in Titanium Alloys." Fizika Metallov I Metallovedenie, Akademija Nauk SSSR, RU, No. 4, Jan. 1, 1990, pp. 152-158.
Kim, Sun-Ki, Han-Sol Kim, and Won-Yong Kim. "Dry Sliding Wear Characteristics of Ti-Nb-Si Alloys for Biomedical Application." Materials Science Forum, vol. 569, 2008, pp. 149-152.
Inoue, A., H.M. Kimura, T. Masumoto, C. Suryanarayana, A. Hoshi. "Superconductivity of Ductile Ti-Nb-Si Amorphous Alloys." Journal of Applied Physics, vol. 51, Issue 10, Oct. 1980, pp. 5475-5482. Abstract Only.
Kim, Han-Sol and Won-Yong Kim. "Mechanical Properties and Elastic Modulus of Metastable Ti-Nb Based Alloys With Si Addition." Materials Science Forum, vols. 546-549, 2007, pp. 1427-1430.
Kim, Won-Yong, Han-Sol Kim, and In-Dong Yeo. "Low Elastic Modulus β Ti-Nb-Si Alloys for Biomedical Applications." Materials Science Forum, vols. 510-511, 2006, pp. 858-861.
Won-Yong Kim. "Microstructure and Pseudoelasticity of Ti-Nb-Si Based Alloys With Biocompatible Alloying Elements." Materials Science Forum, vols. 546-549, 2007, pp. 2151-2156.

* cited by examiner

*Primary Examiner* — Deborah Yee
(74) *Attorney, Agent, or Firm* — Roberts & Roberts, LLP

(57) ABSTRACT

A titanium based, ceramic reinforced alloy ingot for use in producing medical implants. An ingot is formed from an alloy having comprising from about 5 to about 35 wt. % niobium, from about 0.5 to about 3.5 wt. % silicon, and from about 61.5 to about 94.5 wt. % of titanium. The alloy has a hexagonal crystal lattice α phase of from about 20 vol % to about 70 vol %, and a cubic body centered β crystal lattice phase of from about 30 vol. % to about 80 vol. %. The ingot has an ultimate tensile strength of about 940 MPa or more, and a Young's modulus of about 150 GPa or less. A molten substantially uniform admixture of a niobium, silicon, and titanium alloy is formed, cast into a shape, and cooled into an ingot. The ingot may then be formed into a medical implant and optionally annealed.

20 Claims, No Drawings

TITANIUM BASED CERAMIC REINFORCED ALLOY FOR USE IN MEDICAL IMPLANTS

BACKGROUND OF THE INVENTION

1. Field of the Invention

The invention relates to a titanium based, ceramic reinforced alloy ingot for use in producing medical implants. More particularly, the invention pertains to a ceramic reinforced alloy ingot comprising titanium, niobium and silicon. The alloy has both an α crystal phase and a β crystal phase. The ingot has an ultimate tensile strength of about 940 MPa or more, and a Young's modulus of about 150 GPa or less.

2. Description of the Related Art

There is great commercial interest in the production of biocompatible, medically suitable implants for surgically jointing bone and implanting teeth. Medical implants such as screws, pins, rods, bars, springs, coils, cables, staples, clips, plates and the like require materials with very high tensile strength and high cyclic fatigue life while also having a modulus of elasticity low enough to be compatible with bone. Common alloys include titanium, stainless steel and cobalt chrome alloys. Stainless steel and cobalt chrome alloys exhibit very high tensile strength, but both contain nickel and chromium which are known irritants to the body. In addition, these alloys have low ductility and a Young's modulus approaching five times that of bone. This high tensile strength and Young's modulus also makes it difficult to machine these components cost effectively using conventional techniques. Titanium and its alloys are especially popular choices for orthopedic bone screws and plates commonly used for spinal fixation. Titanium alloys for a variety of applications are known in the art and there are numerous literature references disclosing a wide range of elements which are used to provide alloys having desired characteristics, such as increased tensile strength and ductility. Generally, titanium and its alloys may exist in one or a mixture of two basic crystalline structures, namely the α phase, which is a hexagonal close-packed structure, and the β phase which is a body-centered cubic structure. The commercially pure grades of titanium alloys have low tensile strengths but show no signs of tissue irritation. These alloys are commonly used for orthopedic plates which are implanted externally to the bone structure and can therefore have a larger size. $Ti_6AlV_4$ alloys are commonly used for higher strength applications such as fixation screws or plates which must be contained in a small area. One known medically implantable alloy is disclosed in U.S. Pat. No. 6,752,882. It provides a biocompatible low modulus, high strength titanium-niobium alloy containing α phase as a major phase and consisting essentially of 10-30 wt % of Nb and the balance titanium. U.S. Pat. No. 5,954,724 relates to titanium alloys suitable for use for medical implants and devices having a high-strength, low-modulus, and high hardness with improved corrosion resistance due to the addition of hafnium and molybdenum, and which additionally allow for surface hardening of an implant made of this alloy. U.S. Pat. No. 7,892,369 provides a method for modifying the microstructure of titanium alloys for use in the manufacture of orthopedic prostheses. An orthopedic prosthesis is initially formed from a titanium alloy and subsequently subjected to a thermal treatment followed by rapid quenching. The microstructure of the titanium alloy in the prosthesis has improved resistance to fretting fatigue. U.S. Pat. No. 7,682,473 provides an implant prosthesis composed of a TiAlNb alloy having a modulus near that for bone to prevent stress shielding, and a tensile and compressive strength and fracture toughness equal to or greater than that of bone. A key problem with other alloys which use aluminum and vanadium is the suspected effect of Al and V when movement and fretting are involved. The release of Al and V into the blood stream could cause irritation for the patient in the long term. Another issue with certain grades of titanium is the so called "notch effect" during cyclic fatigue. Prepared and polished samples of certain titanium alloys have been shown to have fatigue strength near the ultimate tensile strength. However, when a notch is introduced to the sample, the fatigue strength can be lowered to 40% of the ultimate tensile strength. Since implantable devices must be laser marked with the appropriate tracking information, a notch situation always exists and care must be taken not to exceed the notch fatigue strength.

The problems associated with designing an implantable device are specifically, providing an alloy with high tensile strength, and a marginal Young's modulus that contains no known irritants which can be economically machined with conventional methods. The present invention addresses all these issues. The invention provides an alloy of titanium, niobium and silicon. Titanium and niobium alloys are known to form alloys with very low Young's modulus (50-80 GPa). A problem with these known alloys is that they do not have sufficient strength for the manufacture of orthopedic devices such as bone plates and fixation screws. This invention overcomes the limitations of conventional alloys by including within a solid solution of the metals, a glassy silicon ceramic which acts to absorb energy during crack propagation and retard dislocations during applied stress. The atomic percent of this glassy silicon ceramic is controlled as to still allow for a moderately low Young's modulus and good formability. The inventive alloy of primarily Ti with the addition of Nb and Si produces alloys which have a complex alpha/beta structure with an amount of glassy material. The resulting alloy has a higher strength then the titanium grades presently used in medical implants while retaining a comparable elastic modulus.

SUMMARY OF THE INVENTION

The invention provides an ingot comprising an alloy, the alloy comprising from about 5 wt. % to about 35 wt. % of niobium, from about 0.5 wt. % to about 3.5 wt. % of silicon, and from about 61.5 wt. % to about 94.5 wt. % of titanium, the alloy having a hexagonal crystal lattice α phase of from about 20 vol % to about 70 vol %, and a cubic body centered β crystal lattice phase of from about 30 vol. % to about 80 vol. %, the ingot having an ultimate tensile strength of about 940 MPa or more, and a Young's modulus of about 150 GPa or less.

The invention also provides a method of forming an ingot which comprises forming a molten alloy comprising a substantially uniform admixture of from about 5 wt. % to about 35 wt. % of niobium, from about 0.5 wt. % to about 3.5 wt. % of silicon, and from about 61.5 wt. % to about 94.5 wt. % of titanium, casting the molten alloy into a shape, and then cooling the shape into an ingot, the alloy having a hexagonal crystal lattice α phase of from about 20 vol % to about 70 vol %, and a cubic body centered β crystal lattice phase of from about 30 vol. % to about 80 vol. %, the ingot having an ultimate tensile strength of about 940 MPa or more, and a Young's modulus of about 150 GPa or less.

DESCRIPTION OF THE INVENTION

An alloy is formed by combining commercially pure quantities of titanium, niobium and silicon. These may be obtained in the form of bars, wires, powders, particles, or any other convenient form. These are then heated until each is molten and blended into a substantially uniform admixture. The amount of titanium may range from about 61.5 wt. % to about 94.5 wt. %, preferably from about 72.5 wt. % to about 92 wt. %, and more preferably from about 78 wt. % to about 88.75 wt. %. The amount of niobium may range from about 5 wt. % to about 35 wt. %, preferably from about 7 wt. % to about 25 wt. %, and more preferably from about 10 wt. % to about 20 wt. %. The amount of silicon may range from about 0.5 wt. % to about 3.5 wt. %, preferably from about 1 wt. % to about 2.5 wt. %, and more from about 1.25 wt. % to about 2 wt. %. Preferably the alloy has no more than 2 wt. % of nitrogen, oxygen, or carbon. More preferably the alloy has about 1 wt. % or less of nitrogen, oxygen or carbon. Still more preferably the alloy has about 0.5 wt. % or less of nitrogen, oxygen or carbon. In a most preferred embodiment, the alloy comprises only these three elements such that the alloy has from about 5 wt. % to about 35 wt. % of niobium, from about 0.5 wt. % to about 3.5 wt. % of silicon, and the balance being titanium, apart from incidental impurities.

A method for preparing such a high strength, low modulus, biocompatible titanium alloy involves mechanically blending the above components, and then heating them until melted, one or more times.

The alloys are preferably made by mechanically blending accurately weighed portions of the pure elements and melting the blend in a furnace such as a plasma arc furnace or vacuum arc furnace, and remelting as necessary to achieve uniformity, and then casting and cooling. One example of a method of melting includes combining the components in a commercially available arc-melting vacuum pressure casting system. A melting chamber is first evacuated and purged with an inert gas such as argon. An argon pressure of, for example 1.5 kgf/cm² may be maintained during melting. The appropriate amounts of titanium, niobium and silicon are prepared by electron beam skull melting with induction stirring of the melt. The resulting mixture may optionally be re-melted multiple times to improve homogeneity. The molten alloy is then cast, or drawn out of the crucible by a water cooled rod to form a cylindrical ingot, with cooling. The alloy has a combination crystal lattice structure of both α and β phases. In particular, the alloy has a hexagonal crystal lattice α phase of from about 20 vol % to about 70 vol %, and a cubic body centered β crystal lattice phase of from about 30 vol. % to about 80 vol. %. Preferably the alloy has a hexagonal crystal lattice α phase of from about 40 vol. % to about 70 vol. %, and a cubic body centered β crystal lattice phase of from about 30 vol. % to about 60 vol. %. More preferably the alloy comprises a hexagonal crystal lattice α phase of from about 45 vol. % to about 65 vol. %, and a cubic body centered β crystal lattice phase of from about 45 vol. % to about 60 vol. %.

The resulting ingot has an ultimate tensile strength of about 940 MPa or more, usually from about 1000 MPa to about 1400 MPa, and more usually from about 1100 MPa to about 1300 MPa. The resulting ingot has a Young's modulus of about 150 GPa or less, usually from about 100 GPa to about 150 GPa, and more usually from about 110 GPa to about 140 GPa.

The resulting ingot may then be formed into the desired medial implant shape, such as those in the form of a screw, pin, rod, bar, spring, coil, cable, staple, clip, plate, or the like. The implant may also be form into customized shapes such as those conforming to hip joint stems, femoral heads, knee femoral components, knee tibial components, intramedullary nails, inner ear vent tubes, spinal plates, spinal disks, pelvic plates, dental implants, cardiovascular implants, compression hip screws, and the like. Such forming may be done by the use of customary machine tooling. Optionally either the cast ingot or the machined medical implant may be annealed for additional strength, polished or anodized by well known methods. Annealing may be done by heating at temperatures ranging from about 500° C. to about 1200° C., preferably from about 750° C. to about 1000° C., for from about 20 minutes to about 360 minutes, preferably from about 40 minutes to about 120 minutes. Polishing may be done by mechanical burnishing. Anodizing may be done by electrochemically oxidizing the surface.

The following non-limiting examples serve to illustrate the invention.

EXAMPLES

Three alloys were formed and tested in both the as cast condition, and after annealing at 950° C. for 1 hour in vacuum. The alloys were prepared by electron beam skull melting with induction stirring or the melt. The resulting material was drawing out of the crucible by a water cooled rod to form a cylindrical ingot.

| Alloy Test | Condition | Nb | Si | UTS (Mpa) | Young's Modulus (GPa) | Yield Strength (Mpa) | Elongation (%) |
|---|---|---|---|---|---|---|---|
| 1 | As Cast | 10 | 1.1 | 1012 | 113 | 940 | 4.6 |
| 2 | As Cast | 13 | 1.5 | 995 | 112 | 937 | 6.2 |
| 3 | As Cast | 21 | 1.25 | 1022 | 110 | 960 | 4.8 |
| 1a | Annealed | 10 | 1.1 | 1006 | 81 | 945 | 4.5 |
| 2a | Annealed | 13 | 1.5 | 1008 | 83 | 957 | 3.3 |
| 3a | Annealed | 21 | 1.25 | 957 | 76 | 850 | 3.25 |

The sample ingots were subjected to machinability tests, polishing tests and color anodizing. The composition performed excellently in all cases, with the polishing and anodizing exceeding the characteristics of commercially available Grade 4 and Grade 23 titanium. Detailed chemical and phase analysis of the Ti-21Nb-1.25Si material was performed. The phase analysis shows a roughly 55/45 alpha/beta structure. XPS analysis confirmed that there existed a large number of atoms in a glassy phase with 1.6 at % of the material existing as SiC. This SiC glassy ceramic is deposited at the grain boundaries. Given the high fracture toughness of the carbide these interstitial components act not only prohibit dislocation movement but also absorb energy in the case of crack propagation. The presence of carbon in the alloy used to form the SiC is present in the starting raw material as a typical impurity.

While the present invention has been particularly shown and described with reference to preferred embodiments, it will be readily appreciated by those of ordinary skill in the art that various changes and modifications may be made without departing from the spirit and scope of the invention. It is intended that the claims be interpreted to cover the disclosed embodiment, those alternatives which have been discussed above and all equivalents thereto.

What is claimed is:

1. An ingot comprising an alloy, the alloy comprising from about 5 wt. % to about 35 wt. % of niobium, from about 0.5 wt. % to about 3.5 wt. % of silicon, and from about 61.5 wt. % to about 94.5 wt. % of titanium, the alloy having a hexagonal crystal lattice α phase of from about 20 vol % to about 70 vol %, and a cubic body centered β crystal lattice phase of from about 30 vol. % to about 80 vol. %, the ingot having an ultimate tensile strength of about 1,000 MPa or more, and a Young's modulus of about 150 GPa or less.

2. The ingot of claim 1 wherein the alloy comprises from about 5 wt. % to about 35 wt. % of niobium, from about 0.5 wt. % to about 3.5 wt. % of silicon, and the balance titanium.

3. The ingot of claim 1 wherein the alloy comprises from about 7 wt. % to about 25 wt. % of niobium, from about 1 wt. % to about 2.5 wt. % of silicon, and from about 72.5 wt. % to about 92 wt. % of titanium.

4. The ingot of claim 1 wherein the alloy comprises from about 10 wt. % to about 20 wt. % of niobium, from about 1.25 wt. % to about 2 wt. % of silicon, and from about 78 wt. % to about 88.75 wt. % of titanium.

5. The ingot of claim 1 which has an ultimate tensile strength of from about 1000 MPa to about 1400 MPa, and a Young's modulus of from about 100 GPa to about 150 GPa.

6. The ingot of claim 1 which has an ultimate tensile strength of from about 1100 MPa to about 1300 MPa, and a Young's modulus of from about 110 GPa to about 140 GPa.

7. The ingot of claim 1 wherein the alloy has no more than 2 wt. % of nitrogen, no more than 2 wt. % of oxygen, and no more than 2 wt. % of carbon.

8. The ingot of claim 1 wherein the alloy has about 1 wt. % of nitrogen or less, about 1 wt. % of oxygen or less, and about 1 wt. % of carbon or less.

9. The ingot of claim 1 wherein the alloy has about 0.5 wt. % of nitrogen or less, about 0.5 wt. % of oxygen or less, and about 0.5 wt. % of carbon or less.

10. The ingot of claim 1 wherein the alloy comprises a hexagonal crystal lattice α phase of from about 40 vol. % to about 70 vol. %, and a cubic body centered β crystal lattice phase of from about 30 vol. % to about 60 vol. %.

11. The ingot of claim 1 wherein the alloy comprises a hexagonal crystal lattice α phase of from about 45 vol. % to about 65 vol. %, and a cubic body centered β crystal lattice phase of from about 45 vol. % to about 60 vol. %.

12. A medical implant formed from the ingot of claim 1.

13. The medical implant of claim 12 which is in the form of a screw, pin, rod, bar, spring, coil, cable, staple, clip or plate.

14. A method of forming an ingot which comprises forming a molten alloy comprising a substantially uniform admixture of from about 5 wt. % to about 35 wt. % of niobium, from about 0.5 wt. % to about 3.5 wt. % of silicon, and from about 61.5 wt. % to about 94.5 wt. % of titanium, casting the molten alloy into a shape, and then cooling the shape into an ingot, the alloy having a hexagonal crystal lattice α phase of from about 20 vol % to about 70 vol %, and a cubic body centered β crystal lattice phase of from about 30 vol. % to about 80 vol. %, the ingot having an ultimate tensile strength of about 940 MPa or more, and a Young's modulus of about 150 GPa or less.

15. The method of claim 14 wherein the alloy comprises from about 5 wt. % to about 35 wt. % of niobium, from about 0.5 wt. % to about 3.5 wt. % of silicon, and the balance being titanium.

16. The method of claim 15 further comprising the subsequent step of forming the ingot into a medical implant.

17. The method of claim 16 wherein the medical implant is in the form of a screw, pin, rod, bar, spring, coil, cable, staple, clip or plate.

18. The method of claim 15 further comprising the subsequent step of annealing the ingot.

19. The method of claim 16 further comprising the subsequent step of annealing the medical implant.

20. The method of claim 14 wherein the alloy has no more than 2 wt. % of nitrogen, no more than 2 wt. % of oxygen, and no more than 2 wt. % of carbon.

* * * * *